(12) United States Patent
Erickson

(10) Patent No.: US 7,295,876 B1
(45) Date of Patent: Nov. 13, 2007

(54) SYSTEM AND METHOD FOR GENERATING AND TESTING TREATMENT PROTOCOLS

(75) Inventor: John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 168 days.

(21) Appl. No.: 11/072,998

(22) Filed: Mar. 4, 2005

Related U.S. Application Data

(60) Provisional application No. 60/550,039, filed on Mar. 4, 2004.

(51) Int. Cl.
*A61N 1/18* (2006.01)
(52) U.S. Cl. ............... 607/46; 607/2; 607/30; 607/31; 607/43; 607/60
(58) Field of Classification Search ............ 607/30–31, 607/60, 46, 2, 43
See application file for complete search history.

(56) References Cited

U.S. PATENT DOCUMENTS

| | | | |
|---|---|---|---|
| 5,938,690 A * | 8/1999 | Law et al. ............. | 607/46 |
| 6,205,359 B1 * | 3/2001 | Boveja ................. | 607/45 |
| 6,393,325 B1 * | 5/2002 | Mann et al. ........... | 607/46 |
| 6,609,031 B1 * | 8/2003 | Law et al. ............. | 607/46 |
| 2004/0215286 A1 * | 10/2004 | Stypulkowski ......... | 607/48 |

* cited by examiner

*Primary Examiner*—Carl Layno
*Assistant Examiner*—Shevon E Johnson
(74) *Attorney, Agent, or Firm*—Peter R. Lando; Christopher S. L. Crawford

(57) ABSTRACT

A system, method, and computer program product for interactively defining and calibrating a treatment protocol program for a stimulation device such as an implantable pulse generator (IPG). An IPG, whether it is a self-contained implantable pulse generator (SCIPG) or externally-powered implantable pulse generator (EPIPG), communicates with an external patient programmer (EPP) to receive treatment protocol programs. Using the EPP, treatment protocol programs are developed, executed, and tested while the patient provides real-time feedback, providing efficient and effective programming.

22 Claims, 2 Drawing Sheets

SYSTEM AND METHOD FOR GENERATING AND TESTING TREATMENT PROTOCOLS

CROSS-REFERENCE TO RELATED APPLICATIONS

This application claims priority benefit of U.S. Provisional Patent Application No. 60/550,039 entitled "SYSTEM AND METHOD FOR GENERATING AND TESTING TREATMENT PROTOCOLS," filed Mar. 4, 2004, the disclosure of which is hereby incorporated herein by reference. This application is related to concurrently filed "SYSTEM AND METHOD FOR STIMULUS CALIBRATION FOR AN IMPLANTABLE PULSE GENERATOR", Ser. No. 11/073,026, the disclosure of which is hereby incorporated herein by reference.

TECHNICAL FIELD OF THE INVENTION

The present invention is directed, in general, to medical devices and, more specifically, to neurostimulation devices.

BACKGROUND OF THE INVENTION

The present invention relates to stimulation systems, for example, spinal cord, peripheral, and deep-brain stimulation systems. A spinal cord stimulation system is an implantable pulse generating system used to provide electrical stimulation pulses from an electrode array placed epidurally or surgically near a patient's spine. An implanted pulse generator (IPG) may operate independently to provide the required electrical stimulation, or may interact with an external programmer, which delivers programming and/or control information and/or energy for the electrical stimulation, typically through a radio-frequency (RF) or other wireless signal.

Spinal cord stimulation (SCS) is a well-accepted clinical method for reducing pain in certain populations of patients. SCS systems typically include an implanted device, lead wires, and electrodes connected to the lead wires. The implanted device receives signals from an external programmer, and transmits corresponding electrical pulses that are delivered to the spinal cord (or other tissue) through the electrodes which are implanted along the dura of the spinal cord. In a typical situation, the attached lead wires exit the epidural space and are tunneled around the torso of the patient to a subcutaneous pocket where the device is implanted.

Spinal cord and other stimulation systems are known in the art. For example, in U.S. Pat. No. 3,646,940, there is disclosed an implantable electronic stimulator that provides timed, sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neurostimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means for generating electrical stimulations and must be coupled to the external controller in order for neurostimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 5,121,754; 5,417,719, 5,501,703, and 6,516,227. All of the patents noted above are hereby incorporated by reference.

A typical IPG is self contained, having a multi-year battery pack and a single treatment program, and is generally programmed during or immediately following implantation in the patient's body.

Other SCS systems have no implanted power source, but receive power and programming and/or control information from an external transmitter. These systems will convert the RF signals from the transmitter to provide power to the implanted receiver, and use the RF programming information to determine the intensity, location, and duration of the electrical pulses delivered to the electrodes.

There is a significant programming limitation with known SCS systems. In a typical IPG, the patient's program is installed during implantation, and the patient must visit a doctor to have any programming changes made.

During this initial or follow-up programming session, there is currently no easy way to develop and calibrate treatment protocols. Current methods require an IPG program to be manually configured, downloaded, and then tested on the patient. If the program is not optimal, the entire process must be repeated.

In U.S. Pat. No. 6,393,325, also incorporated by reference, a system for programming an IPG is shown. In this system, a user can select between multiple individual stimulation settings. Here, while a stimulation is continually applied, the user can manually switch from one electrode combination to another. Also, while a stimulation is continually applied, the user can adjust pulse width and frequency, and can adjust the amplitude of the stimulation current. Finally, while a stimulation is continually applied, the user can use directional arrows to change the electrode configuration in an attempt to "direct" the stimulation to affect a particular area of the body. In each of these cases, only one stimulation setting/electrode configuration appears to be used at a time, so the user is limited to treating "simple" pain, in only one area of the body.

There is, therefore, a need in the art for an improved system, process and device for improved interactive programming for IPGs.

SUMMARY OF THE INVENTION

In one embodiment of the present invention, there is a system and methods for interactively defining and calibrating a treatment protocol program for stimulation systems such as, for example, implantable pulse generators.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art will appreciate that they may readily use the conception and the specific embodiment disclosed as a basis for modifying or designing other structures for carrying out the same purposes of the present invention. Those skilled in the art will also realize that such equivalent constructions do not depart from the spirit and scope of the invention in its broadest form.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION OF THE INVENTION

FIGS. 1 through 4, discussed below, and the various embodiments used to describe the principles of the present invention in this patent document are by way of illustration only and should not be construed in any way to limit the scope of the invention. Those skilled in the art will understand that the principles of the present invention may be implemented in any suitably arranged device. The numerous innovative teachings of the present application will be described with particular reference to the presently preferred embodiment.

In embodiments of the present invention, there are a system and methods for interactively defining and calibrating a treatment protocol program for a stimulation system such as, for example, an implantable pulse generator (IPG). The IPG, whether it is a self-contained implantable pulse generator (SCIPG) or externally-powered implantable pulse generator (EPIPG), communicates with an external patient programmer (EPP) to receive treatment protocol programs. Using the EPP, treatment protocol programs are developed, executed, and tested while the patient provides real-time feedback, providing efficient and effective programming.

As used herein, an SCIPG is an IPG having an implanted power source, such as a long-lasting or rechargeable battery. An EPIPG is an IPG which receives at least some of its operating power from an external power transmitter, preferably in the form of a RF signal. The external power transmitter, in the preferred embodiment, is built into the EPP.

Figure 1:
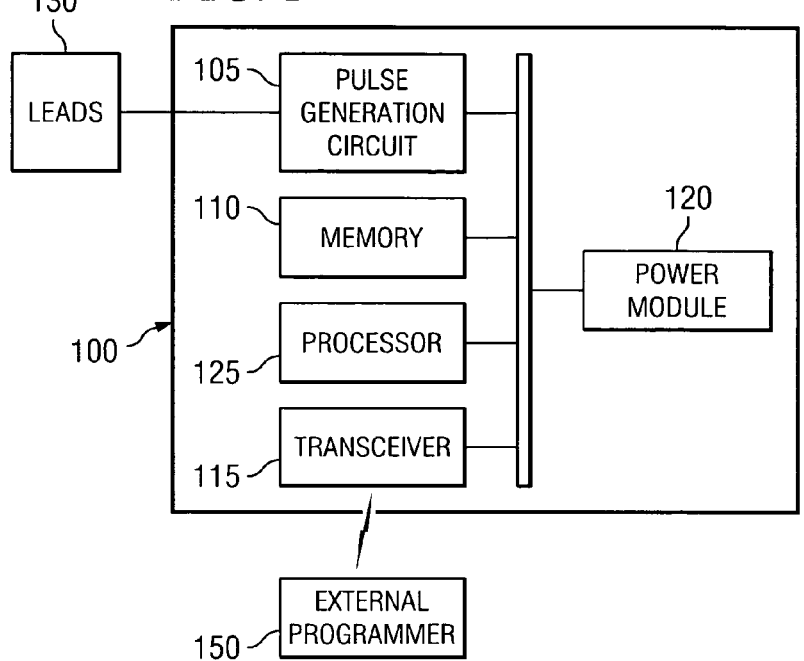
FIG. 1 depicts a block diagram of an implantable pulse generator in accordance with a preferred embodiment of the present invention.

FIG. 1 shows a diagram of the components of an IPG 100 in accordance with the preferred embodiment. The implanted device comprises, but is not limited to, a pulse generation circuit 105, a non-volatile memory 110, a transceiver 115, a power module 120, and a processor 125. Memory 110 may also include volatile memory (not shown).

In an SCIPG, the power module 120 will include a long-term battery or a rechargeable battery and a voltage detection and regulation circuit. In an EPIPG, and in an SCIPG with a rechargeable battery, the power module 120 will include a circuit for converting radio-frequency (RF) energy (or other energy) into direct current. In either case, the power module 120 is connected to power the processor 125 and the pulse generation circuit 105.

One example of an SCIPG may be an SCIPG manufactured by Advanced Neuromodulation Systems, Inc. such as the Genesis® system, part number 3608. One example of the EPIPG may be an EPIPG manufactured by Advanced Neuromodulation Systems, Inc. such as the Renew® system, part number 3416.

The pulse generation circuit 105 is connected, to receive power from power module 120 and to be controlled by processor 125. Processor 125 is connected to receive power from power module 120 and to read from, and write to, non-volatile memory 110. Further, processor 125 is connected, to receive and decode data from transceiver 115. Note that in different embodiments, transceiver 115 may only be a receiver, while in preferred embodiments, processor 125 is connected to also transmit data via transceiver 115. Further, in various embodiments, transceiver 115 receives power signals for operating or recharging the IPG, transmits, and receives.

Transceiver 115 is positioned to receive RF commands from an external programmer 150, and to deliver these commands to processor 125. Further, in an EPIPG, the receiver 115 is configured to receive RF power signals, and to deliver these to power module 120.

Non-volatile memory 110 contains programming and control data, and can be written to and read from by processor 125.

Leads 130 are implanted in the patient's epidural space (or other locations), as described above or known to those of skill in the art. Leads 130 connect with pulse generation circuit 105, optionally via lead extensions (not shown).

Leads 130, in one embodiment, have multiple electrodes, each of which can be independently controlled by the pulse generation circuit 105. Each electrode can be individually set as a positive (acting as an anode), a negative (acting as a cathode), or to a high impedance (turned off). The pulse generation circuit 105, under control of the processor 125, also controls the pulse amplitude, pulse width, and pulse frequency to each electrode on the leads 130.

Also shown here, although not a part of the IPG 100 itself, is external programmer 150, which communicates with transceiver 115. External programmer 150 can be either an external patient programmer (EPP), which is typically carried and operated by the patient, or an advanced programmer, which is typically operated by the patient's physician or clinician. External programmer 150 will typically communicate with transceiver 115 via an antenna (not shown), placed on or near the patient's body proximal to the IPG 100, via near-field or far-field technology.

A program comprises one or more stimulation settings, also referred to herein as "stimsets." The programmed stimulation settings specifically define and characterize the administered electric pulse stimulation. Other information related to stimulation settings, applications, and pain management, not necessary for an understanding of the presently preferred embodiments, is found in U.S. Pat. No. 5,938,690, filed 7 Jun. 1996 and issued 17 Aug. 1999, U.S. Pat. No. 6,609,031, filed 7 Jun. 1996 and issued 19 Aug. 2003, and U.S. patent application Ser. No. 10/120,953, filed 11 Apr. 2002 and published 22 Aug. 2002 as United States Patent Application Publication No. 2002/0116036, all of which are hereby incorporated by reference.

In one embodiment, each stimset is comprised of an electrode configuration and stimulation amplitude, stimulation frequency, and/or stimulation pulse width, and those of skill in the art will recognize that other parameters can be included. The electrode configuration defines whether each electrode is on or off and, if on, the polarity of that electrode. The amplitude is the intensity of the applied electric pulse. The frequency is the number of times the electrodes are turned on each second. The pulse width is the amount of time the pulses are left on during each cycle.

A program is defined as having at least one stimset, and generally corresponds to providing a treatment relating to a specific part of a patient's body. A program can have multiple stimsets; in this case, each stimset is applied sequentially, repeatedly, and/or randomly. Preferably, each program is applied so that the patient experiences the combined effect of each stimset, as if they were being applied simultaneously.

For example, a first stimset may provide relief to a patient's right leg, and a second stimset may provide relief to a patient's left leg. According to one embodiment, then, there will be at least three programs stored on the patient's IPG:

Program 1 comprises the first stimset;

Program 2 comprises the second stimset; and

Program 3 comprises both the first and second stimsets.

In this case, when the patient uses program 1 on the IPG, she would feel relief in her right leg, program 2 would provide relief in her left leg, and program 3 would provide relief in both legs.

A program comprising more than one stimset is referred to herein as a "multistim program."

In one embodiment, the IPG is capable of storing up to 24 different programs, each program having up to 8 stimsets. Of course, in other embodiments, the IPG can store a much greater number of programs, each having associated a much greater number of stimsets.

In the preferred embodiment, all active electrodes in a stimset receive the same stimulation input, including the same pulse width, pulse frequency, and pulse amplitude. Each electrode in the stimset is assigned a polarity of positive, negative, or off. For example, a first stimset for an 8-electrode lead can be defined as having an amplitude of approximately 4 mA, delivered with a 280 microsecond pulse width and an 80 Hz frequency, with the following electrode polarities, with "+" indicating a positive polarity (anode), "–" indicating a negative polarity (cathode), and "0" indicates that the electrode is off:

| Electrode # | 0 | 1 | 2 | 3 | 4 | 5 | 6 | 7 |
|---|---|---|---|---|---|---|---|---|
| Polarity | + | + | 0 | 0 | – | – | + | 0 |

Note that in the preferred embodiment, every stimset must have at least one anode and one cathode. In an alternate embodiment, the IPG itself can act as an anode. A second stimset for an 8-electrode lead can be defined as having an amplitude of approximately 4.2 mA, delivered with a 240 microsecond pulse width and an 80 Hz frequency, with the following electrode polarities:

| Electrode # | 0 | 1 | 2 | 3 | 4 | 5 | 6 | 7 |
|---|---|---|---|---|---|---|---|---|
| Polarity | – | – | 0 | + | – | 0 | + | 0 |

Then, if a multistim program contains both the first and second stimset (as the exemplary Program 3, above), as the program is executed, the IPG will rapidly alternate between the first and second stimsets, so that the patient experiences the combined effect of both stimsets in the multistim program. In the currently preferred embodiment, all stimsets in a program are alternated with the same frequency, but other embodiments allow for different stimset alternating frequencies in a single program.

A typical pulse, in a preferred embodiment, is approximately 4V-5V at 4 mA delivered with a 280 microsecond pulse width and an 80 Hz frequency. Those of skill in the art will recognize that the pulse amplitude can also be defined in volts.

Figure 2:
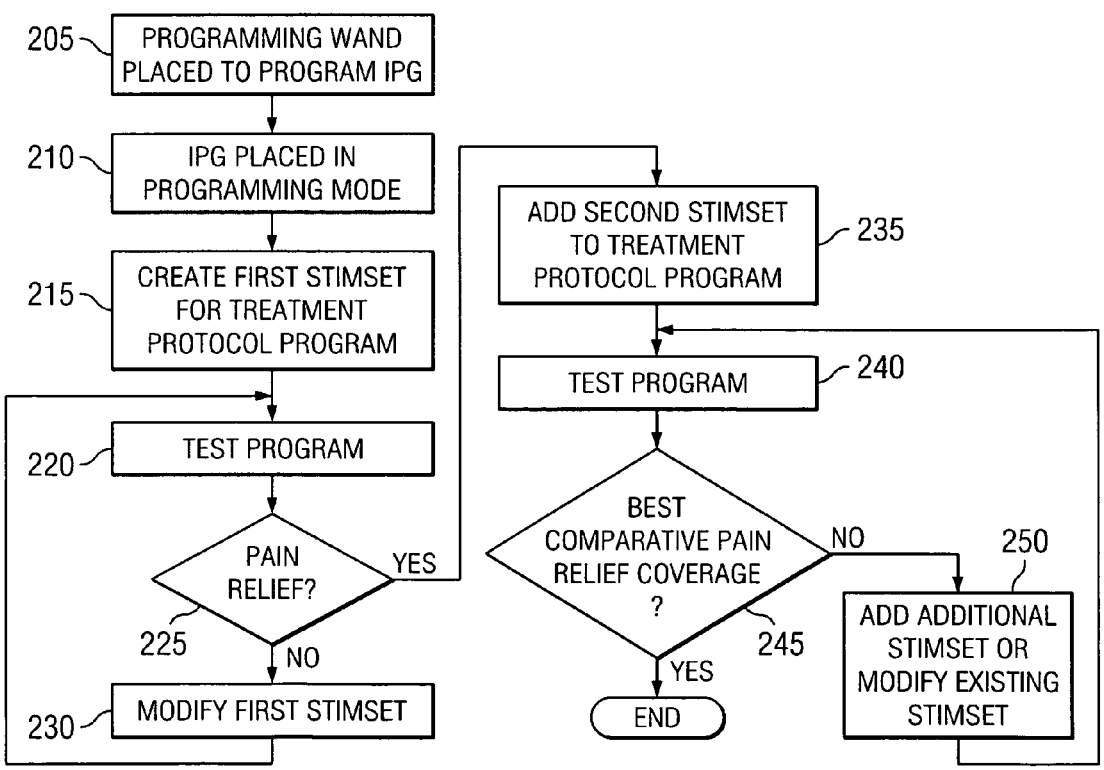
FIG. 2 depicts a flowchart of a process in accordance with a preferred embodiment of the present invention.

FIG. 2 depicts a flowchart of a process for programming the IPG with multiple treatment-protocol programs. Note that this process is used to program an already-implanted IPG; a similar process can be used to pre-program the IPG before implantation.

This process is typically performed by a physician or other professional using an advanced programmer, as described herein. Generally, this programming process is not one that would normally be performed by a patient, but could be so if the patient were properly trained.

First, a programming wand will be placed in a location proximate to the IPG or the IPG antenna (step 205). In other embodiments, "far-field" programming can be used. Next, preferably using an RF signal, the advanced programmer will place the IPG into programming mode (step 210).

The advanced programmer is then used to create a stimset for a treatment protocol program (step 215). The treatment protocol program may be stored in either the IPG or the programmer in certain embodiments of the invention. This program is tested (step 220), and the patient will report whether she is experiencing any pain relief from the stimulation (step 225). If not, the first stimset is modified and the program comprising the modified stimset is tested (step 230, returning to step 220).

If the patient does experience relief, the programmer will then select a second stimset (step 235) for the program, and test the program in step 240. The first and second stimset are alternately used by the tested program in preferred embodiments of the invention. In other embodiments, the first and second stimset are randomly or simultaneously used by the tested program to generate a stimulation in step 240. This enables the IPG to treat "complex" pain in multiple body areas, as each stimset in the tested program can cover a different body area, or can overlap for more complete coverage in a specific area.

In the preferred embodiment, the tested program comprising a first and a second stimset is sent to the IPG and executed. A decision is then made in step 245 by receiving a patient selection as to whether the tested program provides the best comparative pain relief. If the tested program does not provide the best comparative pain relief, then additional stimsets are added to the program or existing stimsets are modified in step 250. The program is then tested as before in step 240. In certain embodiments, more than one program is generated by the process described above, and the separate programs are compared to each other. Steps 235-250 continue until an acceptable program is generated.

It should be noted that, in the preferred embodiment, the stimulation is actually stopped momentarily a program is modified and tested, such as, for example, when additional stimsets are added. Further, this approach differs from known methods in particular by using multistim programs, where known methods are limited to testing a single stimset at a time.

Note that, optionally, the new secondary stimset in the test multistim program can either replace one of the stimsets in the program, or can be added as an additional stimset in the test multistim program. Thus, the test multistim program can include as few as two stimsets up to as many as eight stimsets, in the preferred embodiment, or even more in alternate embodiments. Of course, a program can consist of only one stimset, but then it is not an actual "multistim" program.

According to the process above, a multistim treatment program can be quickly developed using a technique similar to the process used in determining an eyeglass prescription. A series of tests are made wherein the "best-so-far" multistim program is compared against a test multistim program, and the patient merely has to indicate which of the two feels better. The better of the two is stored, and used against a new test multistim program in the subsequent comparison.

Here, the test multistim programs can be individually programmed by the operator of the programmer, or can be automatically generated by the programmer. In either case, the operator will simply indicate whether program "A" or program "B" is selected as the new "best-so-far" multistim program, according to the patient's feedback.

When the patient indicates that full-coverage relief has been achieved, or the operator otherwise determines that the best practical coverage has been achieved, the process will end and the current "best-so-far" or known-good program is stored to the patient's IPG.

Figure 3:
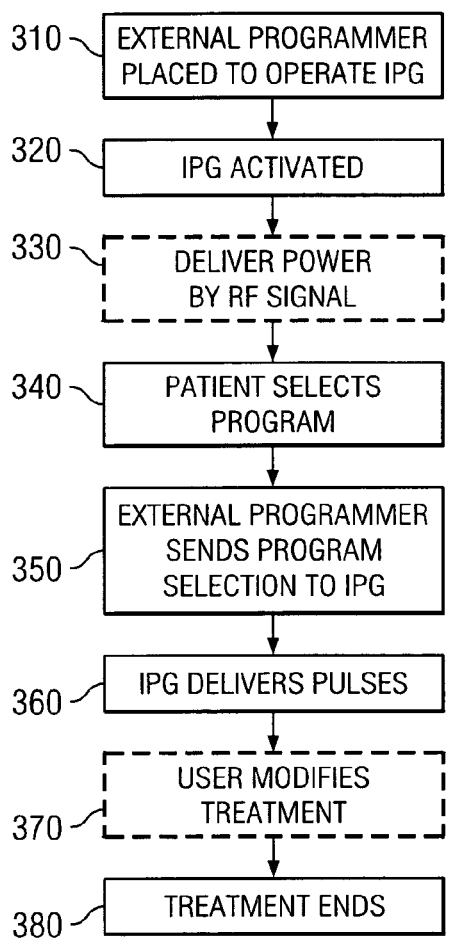
FIG. 3 depicts a flowchart of a process in accordance with a preferred embodiment of the present invention.

FIG. 3 depicts a flowchart that describes the use of an IPG having multiple treatment-protocol programs stored within. This process is generally performed by the patient.

First, the external programmer will be placed in a location proximate to the IPG or the IPG antenna (step 310). Next, preferably using an RF signal, the advanced programmer will activate the IPG (step 320).

During operation, the external programmer will optionally, as in the case of an EPIPG, supply power to the IPG, preferably using an RF signal (step 330). The patient will select the treatment protocol on the external programmer (step 340), and the external programmer will send an RF signal to the IPG to indicate the selected treatment-protocol program (step 350). Alternately, if a treatment protocol selection is not sent by the external programmer, the IPG will select one of the stored treatment-protocol programs as the "default" program.

The IPG delivers the pulse stimulus, as described herein, according to the selected treatment-protocol program (step 360) and its associated stimsets. Optionally, the user can modify the intensity or other aspects of the treatment as needed, using the external programmer (step 370). For example, a typical modification is to change the intensity setting using the external programmer, causing the IPG to adjust the pulse amplitude delivered to the lead electrodes.

When the treatment program is completed, or when the user chooses, the pulse-stimulus treatment ends (step 380).

Another feature of a preferred embodiment is the ability to calibrate a multistim program, whether or not the multistim program was developed using the processes described above. This feature uses a real-time patient feedback process to individually balance specific stimsets in a multistim program, to achieve greater relief for the patient. In a preferred embodiment, the amplitude of the stimset pulse is adjusted, but in other embodiments, other aspects of the pulse can be adjusted as well.

Figure 4:
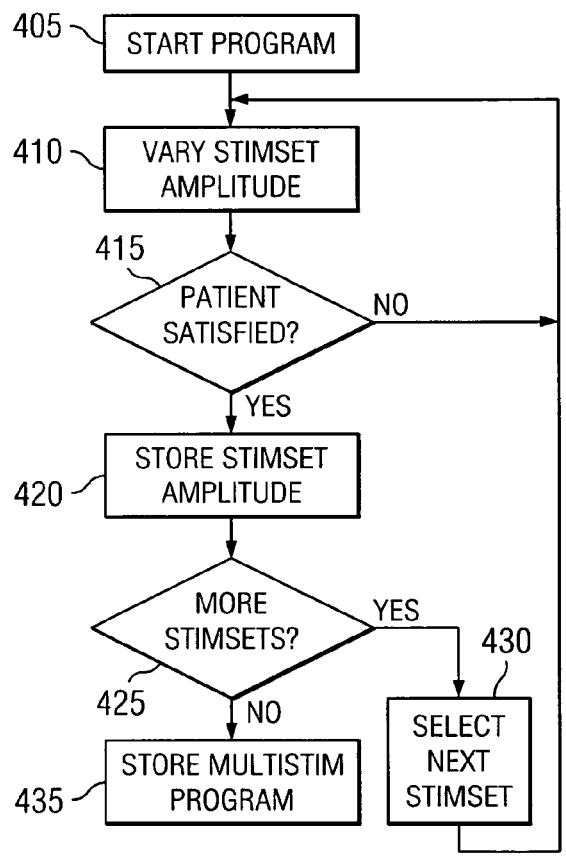
FIG. 4 depicts a flowchart of a process in accordance with a preferred embodiment of the present invention.

FIG. 4 depicts a flowchart in accordance with a preferred embodiment of the present invention. This process is preferably performed using an advanced programmer, by a physician or other trained practitioner.

First, a multistim program is executed (step 405) under real control of the advanced programmer, operating a patient's IPG. As described above, this multistim program comprises a plurality of stimulation settings (stimsets) that are applied in sequence, repeatedly.

Next, as the multistim program is executing, the amplitude of one of the stimsets of the multistim program is varied (step 410). This continues, varying the amplitude between minimum and maximum thresholds, until the patient indicates when the most positive effect is achieved (step 415). When the patient does so indicate, the current amplitude setting for that stimset is stored (step 420), and remains in use at that setting as the process continues.

If there are remaining stimsets that have not been calibrated (step 425), the next stimset is selected (step 430) and the process repeats at step 410. When one or more, but preferably all, of the stimsets have been calibrated, the multistim program has been optimized, and is stored (step 435), including all of the new amplitude settings for each stimset.

It should be noted that in a preferred embodiment of this process, the stimulation is not continually applied during the multistim calibration process. Instead, the stimulation is momentarily stopped as the amplitude of the stimset is adjusted, then the multistim stimulation is reapplied with the new amplitude settings.

Further, while the preferred embodiment provides that all electrodes of each stimset of a multistim program operate with the same pulse width, frequency, and amplitude, in other embodiments, each of these parameters can be adjusted independently.

Those skilled in the art will recognize that, for simplicity and clarity, the full structure and operation of all devices and processes suitable for use with the present invention is not being depicted or described herein. Instead, only so much of an implantable pulse generator and supporting hardware as is unique to the present invention or necessary for an understanding of the present invention is depicted and described. The remainder of the construction and operation of the IPGs described herein may conform to any of the various current implementations and practices known in the art.

Those of skill in the art will also recognize that not all steps in the above-described processes must be performed in the order described. Further, not all steps of any process, particularly the optional steps, must necessarily be performed in conjunction with all other steps, and can be omitted from the process or performed independent of other steps of the process.

It is important to note that while the present invention has been described in the context of a fully functional system, those skilled in the art will appreciate that at least portions of the mechanism of the present invention are capable of being distributed in the form of an instruction set contained within a machine usable medium in any of a variety of forms, and that the present invention applies equally regardless of the particular type of instruction or signal bearing medium utilized to actually carry out the distribution. Examples of machine usable mediums include: nonvolatile, hard-coded type mediums such as read only memories (ROMs) or erasable, electrically programmable read only memories (EEPROMs), user-recordable type mediums such as floppy disks, hard disk drives and compact disk read only memories (CD-ROMs) or digital versatile disks (DVDs), and transmission type mediums such as digital and analog communication links.

Although an exemplary embodiment of the present invention has been described in detail, those skilled in the art will understand that various changes, substitutions, variations, and improvements of the invention disclosed herein may be made without departing from the spirit and scope of the invention in its broadest form.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 U.S.C. § 112 unless the exact words "means for" are followed by a participle.

It may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "control is utilized herein, it means any device, system or part thereof that controls at least one operation, whether such a device is implemented in hardware, firmware, software or some combination of at least two of the same. It should be noted that the functionality associated with any particular controller may be centralized or distributed, whether locally or remotely.

What is claimed is:

1. A method for programming a stimulation device, comprising:
    placing a stimulation device into a programming mode using an external programming device, the external programming device adapted to control the stimulation device;
    sending a treatment protocol program from the external programming device to the stimulation device, wherein the treatment protocol program is associated with a first stimulation setting;
    testing the treatment protocol program using the stimulation device;
    modifying said first stimulation setting according to said testing until pain relief is experienced;
    adding a second stimulation setting to said treatment protocol program to form a test treatment protocol program which stimulates using parameters from each stimulation setting;
    testing said test treatment protocol program; and
    receiving a user selection of a treatment protocol program that provides the best comparative pain relief;
    balancing perceived amplitudes, using the programming device, associated with the first and second stimulation settings in real-time while the treatment protocol program is executed by the stimulation device;
    wherein said test treatment program alternates stimulation settings during said testing and balancing.

2. The method of claim 1 wherein said stimulation device is an implantable pulse generator.

3. The method of claim 1 wherein said test treatment program alternates stimulation settings randomly.

4. The method of claim 1 wherein said step of adding a second stimulation setting further comprises adding multiple stimulation settings.

5. The method of claim 1 wherein the stimulation is paused before each new stimulation setting is added.

6. The method of claim 1, further comprising automatically generating the second stimulation setting by the external programming device.

7. The method of claim 1, further comprising sending additional stimulation settings until a user selection of an optimal treatment protocol program has been received.

8. The method of claim 1, wherein the user selection of a treatment protocol program is stored in memory in the stimulation device.

9. A method of creating a stimulation program for an implantable pulse generator, the method being performed using an external programming device during a programming mode, comprising:
    controlling the implantable pulse generator to execute a stimulation program by generating electrical pulses according to at least a first stimulation set of the stimulation program;
    adding a second stimulation set to the stimulation program, wherein the first and second stimulation sets define respective electrode combinations that are selected to cause the patient to experience pain relief in distinct regions of the body, wherein the adding the second stimulation set causes the implantable pulse generator to alternately generate electrical pulses according to at least the first and second stimulation sets; and
    modifying at least one stimulation parameter of the second stimulation set while the implantable pulse generator continues to execute the stimulation program.

10. The method of claim 9 wherein the modified stimulation parameter is an electrode configuration.

11. The method of claim 9 wherein the modified stimulation parameter is a pulse characteristic.

12. The method of claim 9 further comprising:
    adding a third stimulation set to the stimulation program.

13. The method of claim 12 wherein the third stimulation set replaces the second stimulation set.

14. The method of claim 12 wherein the implantable pulse generator alternately generates electrical pulses according to at least the first, second, and third stimulation sets.

15. A method of creating a stimulation program for an implantable pulse generator, the method being performed using an external programming device during a programming mode, comprising:
    placing the external programming device into a programming mode;
    during the programming mode, controlling the implantable pulse generator to execute a stimulation program, wherein the stimulation program defines electrical pulses to be generated and delivered by the implantable pulse generator using at least a first stimulation set;
    during the programming mode, communicating a second stimulation set to the implantable pulse generator to be added to the stimulation program, wherein the first and second stimulation sets define respective electrode combinations that are selected to cause the patient to experience pain relief in distinct regions of the body, wherein the adding the second stimulation set causes the implantable pulse generator to alternately generate electrical pulses according to at least the first and second stimulation sets; and during the programming mode, modifying at least one stimulation parameter of the second stimulation set while the implantable pulse generator continues to execute the stimulation program.

16. The method of claim 15 wherein the modified stimulation parameter is an electrode configuration.

17. The method of claim 15 wherein the modified stimulation parameter is a pulse characteristic.

18. The method of claim 17 wherein the pulse characteristic is a pulse amplitude.

19. The method of claim 17 wherein the pulse characteristic is a pulse width.

20. The method of claim 15 further comprising:

during the programming mode, communicating a third stimulation set to the implantable pulse generator to be added to the stimulation program.

21. The method of claim 20 wherein the third stimulation set replaces the second stimulation set.

22. The method of claim 20 wherein the implantable pulse generator alternately generates electrical pulses according to at least the first, second, and third stimulation sets.

* * * * *